United States Patent
Hándal Vega et al.

(10) Patent No.: US 9,765,036 B2
(45) Date of Patent: Sep. 19, 2017

(54) PRODUCTION METHOD FOR PRODUCING N-BENZYL-2-(2-NITRO-1H-IMIDAZOL-1-YL) ACETAMIDE

(71) Applicant: MINISTERIO DE EDUCACIÓN, San Salvador (SV)

(72) Inventors: Erlinda Hándal Vega, San Salvador (SV); Carmen Elena Arias Rivas, Zacatecoluca (SV); Ana Karina Cuchilla De Merlos, Olocuilta (SV)

(73) Assignee: Ministerio De Educacion, San Salvador (SV)

( * ) Notice: Subject to any disclaimer, the term of this patent is extended or adjusted under 35 U.S.C. 154(b) by 0 days.

(21) Appl. No.: 15/033,238

(22) PCT Filed: Nov. 19, 2014

(86) PCT No.: PCT/SV2014/000001
§ 371 (c)(1),
(2) Date: Apr. 29, 2016

(87) PCT Pub. No.: WO2015/076760
PCT Pub. Date: May 28, 2015

(65) Prior Publication Data
US 2016/0289197 A1    Oct. 6, 2016

(30) Foreign Application Priority Data
Nov. 19, 2013   (SV) ................ 2013004584

(51) Int. Cl.
*C07D 233/91*     (2006.01)
(52) U.S. Cl.
CPC ................. *C07D 233/91* (2013.01)

(58) Field of Classification Search
CPC .................................... C07D 233/91
See application file for complete search history.

(56) References Cited

U.S. PATENT DOCUMENTS 6,870,057 B1 *  3/2005  Handal Vega ....... C07D 231/12
                                                        548/344.1

OTHER PUBLICATIONS

Reusch, W. "Hydroxyl Group Substitution" in Alcohol Reactivity. Published May 5, 2013 [online]: Michigan State University [retrieved on Jan. 17, 2017]. Retrieved from <https://www2.chemistry.msu.edu/faculty/reusch/virttxtjml/alcohol1.htm>.*

* cited by examiner

*Primary Examiner* — Michael Barker
*Assistant Examiner* — Amanda L Aguirre
(74) *Attorney, Agent, or Firm* — Ladas & Parry LLP

(57) ABSTRACT

The invention relates to the synthesis of a therapeutic agent which is effective against American trypanosomiasis (Chagas disease) caused by the protozoa *Tripanosoma cruzi* and transmitted by blood-sucking insects of the genera Triatoma or Rhodnius. This synthesis method is carried out in one step, in a solid state. It is a clean, simple, economical, rapid, easily implemented method, does not involve acid or base catalysts in the synthesis process, and is also environmentally friendly. It is a synthesis method for producing N-benzyl-2-(2-nitro-1-H-imidazol-1-yl)acetamide from the N-benzyl-2-hydroxyacetamide and 2-nitro-1H-imidazol reaction mixture, using microwave irradiation as an activation source in order to produce the N-benzyl-2-(2-nitro-1H-imidazol-1-yl)acetamide.

5 Claims, No Drawings

PRODUCTION METHOD FOR PRODUCING N-BENZYL-2-(2-NITRO-1H-IMIDAZOL-1-YL) ACETAMIDE

CROSS-REFERENCE TO RELATED APPLICATION

This U.S. application claims priority under 35 U.S.C. 371 to, and is a U.S. National Phase application of, the International Patent Application No. PCT/SV2014/000001, filed 19 Nov. 2014, which claims priority from SV 2013004584 filed 19 Nov. 2013, the disclosures of which are incorporated in their entirety by reference herein.

STATE OF ART

The molecule N-benzyl-2-(2-nitro-1H-imidazole-1-yl)acetamide is an antiparasitic, antiprotozoal derived from 2-nitro-1H-imidazole with activity against *Trypasonoma Cruzi*, prepared and presented in 1966 by Hoffman-La Roche & Co, patent conceded in 1969.

The synthesis method presented in Lon. Pat. L138, 529, originally used sodium methoxide and methanol, adding 2-nitroimidazole, then N,N-dimethylformamide, the mixture is heated up to 153° C. to remove methanol. After the ester 2-chlorine-methylacetate is heated up to 122° C., a precipitate forms, then the formed mixture is heated up between 105° C. and 115° C. The solvent is evaporated in a bath at 50° C. and then the pressure is reduced 1.2 mm of Hg and the formed solid is recrystallized in ethanol. The ester 2-(2-nitromidazole-(1)-yl)methyl acetate is obtained.

The ester 2-(2-nitromidazole-(1)-yl)methyl acetate is dissolved with benzyl amine in absolute methanol, letting it rest all night long, and then the mixture is refrigerated for many hours. The crystals are collected in fusion point 187.5-189.5° C. The pressured filtered is concentrated and the obtained solid is recrystallized with ethyl acetate to give additional material with fusion point 187.5-189° C. The recrystallization in ethanol gives crystals of N-benzyl-2(2-nitromidazole-(1)-yl)acetamide with fusion 188.5° C.-190° C. and λ max in ethanol 313 mµ.

The patent U.S. Pat. No. 6,870,057 B1 presents the synthesis of the antimycotic biphenylimidazolyl-1-(1)-phenyl methanol. One of the steps of synthesis consists of the reaction in solid state of the biphenylcarbinol with an excess of imidazole, in microwave radiation conditions (850-700 W), 30 minutes, level 4 in the oven.

Gandolfi Donadio, L. et al. Developed new technologies to produce benznidazol. At Tecnointi 2013 11th edition Open Journeys of Development, Innovation and Technology Transfer. 2-4 Jul. 2013, Buenos Aires. Edited by the National Industrial Institute. Buenos Aires, edición, pg. 218, ISBN 978-950-532-202-2. It presents the reactions for the benznidazol synthesis according to the Azo Route, the Imidazolona Route and the 2-methyl-tio-imidazol Route. The last two of them established as the final synthesis step the reaction of the N-benzyl-2-chlorineacetamide and the 2-nitro-1H-imidazol in presence of NaH and using DMF as solvent to obtain the benznidazol. In the described routes by Gandolfi Donadio, L. et al., in imidazole route as in 2 methyl-tio-imidazol route, the three final steps of the synthesis are still being studied, it means, they are still hypothetical steps not proven until the date of the mentioned publication.

Hernández Nuñez, Emanuel et al. Synthesis and in vitro trichomonicidal, giardicidal and amebicidal activity of N-acetamide (sulfonamide)-2-methyl-4-nitro-1H-imidazoles. European Journal of Medicinal Chemistry, 44 (2009) 2975-2984 publish the nucleophilic bimolecular substitution of the N-benzyl-2-chlorineacetamide with the anion 2-methyl-1H-imidazol in presence of a potassium carbonate base and using acetonitrile as solvent. The process happens with the agitation and backflow during 8 hours. Our process differing from the one published by Hernández Nuñez Emanuel, happens with molecular 2 nitro-1H-imidazol, not anionic, because there is any kind of base added and it's realized in absence of any solvent.

DESCRIPTION OF THE INVENTION

The present invention is related to the synthesis of an imidazolic derivative with tripanocide activity. The synthesis procedure takes place in a dry medium; it is a simple, economical, and environmently friendly. The synthesis consists in the PRODUCTION METHOD FOR PRODUCING N-BENZYL-2-(2-NITRO-1H-IMIDAZOL-1-YL)ACETAMIDE. N-benzyl-2-(2-nitro-1H-imidazol-1-yl)acetamide is prepared using as initial materials N-benzyl-2-hydroxyacetamide and 2-nitroimidazole, adding each one of the initial materials in an equimolar relation. The procedure is clean, it happens by mixing both initial materials and activating the mixture by microwaves irradiation to form the N-benzyl-2-(2 nitro-1H-imidazole-1-yl)acetamide. The microwave irradiation can be at 100 watts. The synthesis is rapid and easy to execute. The reaction mixture is purified using a chromatography column, using as a stationary base alumina and as a mobile phase ethyl acetate. The method does not require acid catalysts or bases in the synthesis process.

The procedure in this invention can be used to obtain other imidazolic derivatives such as N-benzyl-2-(1H-imidazol-1-yl) acetamide using as initial materials 1H-imidazol and N-benzyl-2-hydroxyacetamide or 1H-imidazol and N-benzyl-2-chlorinacetamide.

EXECUTION EXAMPLE

In the practice this reaction happens as follow:
i. Mix the N-benzyl-2-hydroxyacetamide with the 2-nitromidazole in equimolar relation. Mix the initial materials in solid state, in absence of an organic or inorganic solvent, put them in a transparent receptable in a microwave oven, in a bath of silica and irradiate it with microwaves (700 W), level 4 to 7 in the oven, for approximately 10 minutes. The reaction mixture is purified through the chromography column, using alumina as a stationary phase and as a mobile phase ethyl acetate. TLC analysis is realized to the result product by infrared spectroscopy and spectrometry of mass.

IR=1156 and 1145 cm$^{-1}$ (N—C, amina terciaria), 1539.3 and 1367 cms$^{-1}$ (C—N, nitro group), 1660.3 cm$^{-1}$ (CO—NH amide), 3275.3 cm$^{-1}$ (NH-amide)

MS=260M$^+$

The invention claimed is:
1. A process for preparation of N-benzyl-2(2-nitro-1H-imidazol-1-yl)acetamide of formula (I):

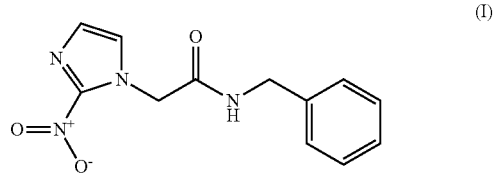 [SMILES: O=C(Cn1ccnc1[N+](=O)[O-])NCc1ccccc1]

comprising reacting N-benzyl-2-hydroxyacetamide (II) and 2-nitro-1H-imidazol (III)

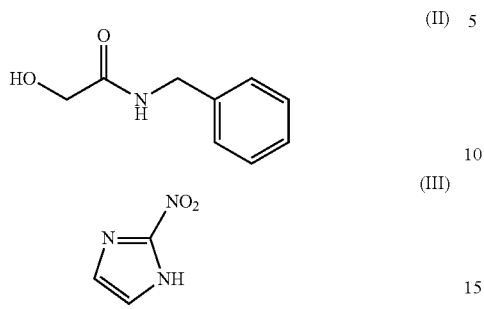

using microwave irradiation.

2. The process according to claim 1, without an excess of any of the reactants.

3. The process according to claim 1, where the reaction is made in solid phase, in absence of a solvent.

4. The process according to claim 1, where the reaction is carried out in absence of a catalyst.

5. The process according to claim 1, wherein the microwave irradiation is at 100 watts.

* * * * *